United States Patent [19]

Sibalis

[11] Patent Number: 4,713,050

[45] Date of Patent: * Dec. 15, 1987

[54] APPLICATOR FOR NON-INVASIVE TRANSCUTANEOUS DELIVERY OF MEDICAMENT

[75] Inventor: Dan Sibalis, Stony Brook, N.Y.

[73] Assignee: Drug Delivery Systems Inc., New York, N.Y.

[*] Notice: The portion of the term of this patent subsequent to Dec. 10, 2002 has been disclaimed.

[21] Appl. No.: 922,518

[22] Filed: Oct. 24, 1986

Related U.S. Application Data

[63] Continuation of Ser. No. 660,192, Oct. 12, 1984, Pat. No. 4,622,031, which is a continuation-in-part of Ser. No. 524,252, Aug. 18, 1983, Pat. No. 4,557,723.

[51] Int. Cl.⁴ .............................................. A61N 1/30
[52] U.S. Cl. ........................................................ 604/20
[58] Field of Search ................. 604/20; 128/798, 802, 128/803, 82.1

[56] References Cited

U.S. PATENT DOCUMENTS

| | | |
|---|---|---|
| 385,567 | 7/1888 | Hoke . |
| 486,902 | 11/1892 | Shults . |
| 588,479 | 8/1897 | Roedel .................................. 604/20 |
| 2,493,155 | 1/1950 | McMillan .............................. 604/20 |
| 2,667,162 | 1/1954 | Zwahlen ................................ 604/20 |
| 2,784,715 | 3/1957 | Kestler ................................... 604/20 |
| 3,163,166 | 12/1964 | Brant et al. ............................ 604/20 |
| 3,289,671 | 12/1966 | Troutman et al. ..................... 604/20 |
| 3,547,107 | 12/1970 | Chapman et al. ..................... 128/640 |
| 4,008,721 | 2/1977 | Burton ................................... 128/798 |
| 4,141,359 | 2/1979 | Jacobsen et al. ....................... 604/20 |
| 4,239,046 | 12/1980 | Ong ....................................... 128/798 |
| 4,243,052 | 1/1981 | Bailey .................................... 128/798 |
| 4,250,878 | 2/1981 | Jacobsen et al. ....................... 604/20 |
| 4,273,135 | 6/1981 | Larimore et al. ...................... 128/20 |
| 4,292,968 | 10/1981 | Ellis ....................................... 604/20 |
| 4,314,554 | 2/1982 | Greatbatch ............................ 604/20 |
| 4,325,367 | 4/1982 | Tapper ................................... 604/20 |
| 4,367,745 | 1/1983 | Welage .................................. 128/798 |
| 4,406,658 | 9/1983 | Lattin et al. ........................... 604/20 |
| 4,419,091 | 12/1983 | Behl et al. ............................. 128/798 |
| 4,474,570 | 10/1984 | Ariure et al. .......................... 604/20 |
| 4,557,723 | 12/1985 | Sibalis ................................... 604/20 |

FOREIGN PATENT DOCUMENTS 2104388  3/1983  United Kingdom ................. 604/20

Primary Examiner—Lee S. Cohen
Attorney, Agent, or Firm—Lackenbach Siegel Marzullo & Aronson

[57] ABSTRACT

An indicator for the electrophoretic deposition of a medicament through or on a skin surface. The device includes layers forming a reservoir containing the drug, a battery layer superimposed on the reservoir, and a cover of electrically conductive material fully enclosing the layers and having a lip along its periphery to electro-conductively engage the skin surface and form an electrical circuit.

6 Claims, 5 Drawing Figures

APPLICATOR FOR NON-INVASIVE TRANSCUTANEOUS DELIVERY OF MEDICAMENT

RELATED U.S. PATENT APPLICATIONS

This is a continuation of application Ser. No. 660,192, filed 10/12/84, now U.S. Pat. No. 4,622,031, which is a continuation-in-part of U.S. patent application Ser. No. 524,252, filed Aug. 18, 1983, now U.S. Pat. No. 4,557,723.

FIELD OF THE INVENTION

This invention relates to electrophoretic transcutaneous drug delivery. Specifically this invention relates to an operating indicator for an electrophoretic transcutaneous drug delivery device.

BACKGROUND OF THE INVENTION AND DISCUSSION OF THE PRIOR ART

The delivery of medicament through a person's skin utilizing electrophoresis is well known where the drug is one whose molecules are ionic in solution or suspension. The solution or suspension is made subject to an electric field and if the electrode having the same charge as that of the ions is above the solution adjacent the skin which is the site of administration, the ions will be repelled and migrate through the skin into the blood stream.

A variety of problems associated with this technique have limited severly the extent of the use of this type of apparatus. Reference to or disclosure of such apparati is shown in the following U.S. Patents, where it will be noted that there is great emphasis in developing electrodes which are disposable and/or more effective:

U.S. Pat. Nos. 2,492,155; 3,163,166; 3,289,671; 3,677,268; 4,141,359; 4,166,457; 4,239,052; 4,243,052; 4,250,878; 4,273,135; 4,367,745.

It will be noted from U.S. Pat. Nos. 3,289,671 and 4,141,359, in particular, that the rate of drug delivery is a function of current flow and that control over current flow is crucial to having the correct amount of medicament applied.

There have also been attempts to provide an apparatus for such electrotherapy which is self-contained, so that the patient can wear the device carrying on normal activities while the drug is being administered. Devices of this type are disclosed in U.S. Pat. Nos. 385,556, 486,902, and 2,784,715.

One problem with such prior art devices was that they were bulky and lacked the necessary drug delivery rate control.

Another significant problem associated with such prior art devices is that the user, in wearing the device, was unable to determine whether the drug was being administered, and more particularly whether the drug was being administered in the proper desired dosage.

Now there is provided by the present invention, an indicator which is formed with a compact electrophoretic drug delivery device so as to positively indicate the flow of the proper dosage of medicament.

SUMMARY OF THE PRESENT INVENTION

An indicator, such as an LCD or an electrochemically phototropic material (ECM) is incorporated into the circuitry of the self-contained electrophoretic device, whereby, when the device is worn in the manner of a bandage and the proper dosage of the drug is being administered, the indicator is activated so as to provide a positive indication of such drug delivery.

This is accomplished in accordance with the principles of this invention by enclosing a complete electrophoretic drug administration system including an indicator within an applicator virtually indistinguishable when in place from an adhesive bandage. The applicator is extremely shallow, capable of being made with a thickness of only about a tenth of an inch, and its length and width would be determined by the desired rate of drug delivery.

One preferred embodiment of this invention consists of a compact, multi-layered applicator having a first active layer containing medicament in contact with the skin, a second active layer superimposed on the first layer comprising a member to make electrical contact with the skin through the first layer, and a third active layer superimposed on the second layer comprising the electrical battery for the applicator in electrical contact with the second layer. Other layers may be included to provide other functions to be described. The assembly just described is enclosed within a cover of electrically conductive material having a lip extending outwardly from the first layer and leaving the latter exposed and in contact with the skin. The underside of the lip is coated with an electrically conductive adhesive material so that when the applicator is mounted on the skin, the cover material surrounded by the lip is in contact with the skin. An LCD, by way of example, is incorporated in the circuitry of the device to serve as an indicator. The lip acts as a return electrode so that the skin completes the electrical circuit when the applicator is applied causing current to flow and medicament to be moved through the skin into the blood stream. With completion of the circuit the indicator is activated.

All of the layers of the applicator may be made from conformable material so that the applicator is capable of being made large enough to be mounted over wide areas regardless of the contour involved.

To insure a constant current flow and a device to terminate drug delivery after a predetermined period of time or quantity of drug, a constant current limiting device is integrally provided in the device.

It is thus a principal object of this invention to provide self-contained apparatus and a method for the electrophoretic deposition of a medicament at a specific, pre-determined, controlled rate, and wherein an indicator provides a positive indicator that the drug is being delivered at the desired controlled rate.

Other objects and advantages of this invention will hereinafter become obvious from the following description of preferred embodiments of this invention.

DESCRIPTION OF THE PREFERRED EMBODIMENTS

Figure 1:
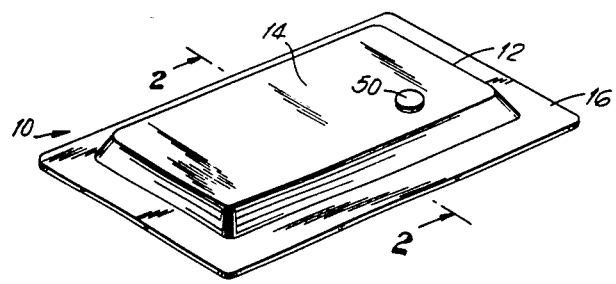
FIG. 1 is a isometric view of an applicator embodying the principles of this invention.
Figure 2:
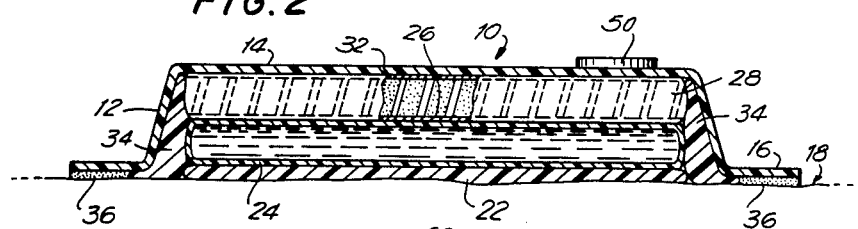
FIG. 2 is a sectional view along line 2—2 of FIG. 1 showing the applicator mounted on skin.

Referring to FIGS. 1 and 2, applicator 10 consists of an outer cover 12 having a raised portion 14 and a lip 16 along the outer periphery. It is understood that applicator 10 can have any convenient shape or size, for example, square, rectangular, oval, circular, or tailored for a specific location on the skin, as long as this is a raised central portion to accommodate the rest of the electrophoresis unit to be described and the lip along its periphery.

As seen in FIG. 2, where applicator 10 is mounted on the surface of skin 18 of a patient, enclosed within the raised portion 14 of cover 12 are several layers to be described. The first layer is a microporous or semipermeable membrane 22 through which the medicament migrates to be deposited on skin 18. As will be noted from the following discussion, membrane 22 may not be needed, depending on the nature of the reservoir for the medicament.

The second layer consists of a flexible pouch or reservoir 24 containing the drug to be administered. As is understood in the art, and shown in one or more of the U.S. patents identified above, reservoir 24 can be a pouch containing the drug of choice in solution or suspension, the walls of which are sufficiently dense to prevent leakage of the drug under ambient conditions, but sufficiently porous to permit migration of the charged particles or ions under the influence of the electric field imposed. It should be noted that it would be appropriate to employ the microporous membrane 22 when leakage under ambient conditions could occur, for example, as a result of packing of the applicators for shipment or storage, fluctuating temperatures, and possibly puncture of the reservoir. Also, the use of the membrane 22 could depend in large measure of the nature of the medicament involved. In the alternative, reservoir 24 can consist of porous material in which the drug is impregnated rather than a pouch containing the liquid medicament.

The third or next layer above reservoir 24 is an extended contact 26 which could be incorporated as one face of battery 28 which is the next layer. Contact 26 could be any suitable conductive material, preferably body-conformable, to permit application 10 so as to be curved or bent to conform to the shaped surface of the skin. Suitable materials of this type are well known in the art and include electrically conductive polymers, preferably non-ionic. Carbon loaded or surface metalized plastics are also available for such use.

Battery 28 comprising the next layer can be made up of a group of cells internally connected in series to obtain the desired voltage necessary to obtain the electrophoretic action with the particular medicament. Orientation of battery 28 would depend on whether the charged (ionic) particles of the drug of choice are positive or negative. If the particles are negatively charged in solution or suspension, then contact 26 would be connected to the negative side of battery 28 as the skin will then be positive with respect to that contact and will attract the ions. With regard to battery 28, it should be noted that any conventional miniaturized battery cells now generally available can be employed, arranged and connected in series to obtain the desired operating voltage. In addition, the technology now exists for batteries which are made up of very thin, flexible sheets of a conductive polymer with high surface areas relative to thickness to provide adequate current desnities. One such co-called plastic battery is described in "Batteries Today", Autumn 1981, pages 10, 11, and 24. When such a battery is employed, sheets may be layered to place the cells in series, and an effective compromise between number of sheets and surface areas of sheets is to layer them in a diagonal as shown somewhat schematically in FIG. 2. Of course, battery selection would ultimately depend on such factors as the degree of conformability desired, voltage and current densities required for a specific application, and time of discharge.

Layered above battery 28 would be another contact 32 which could be similar in construction to that of contact 26 and connected electrically to the opposite side of battery 28.

Cover 12 which encloses all of the layers of applicator 10 is made from a flexible conductive plastic material such as a polymer impregnated with carbon or surface metalized plastic. Insulating material 34 fills the space between the side wall of raised portion 14 and the various layers contained therein.

An electrically conductive adhesive material 36 coats the underside of lip 16 so that applicator or device 10 may be placed on and adhere to skin 18 and make good electrical contact.

It will be seen that the above described arrangement in general forms a complete electric circuit from one side of battery 28, cover 12, adhesive material 36, skin 18, microporous membrane 22, liquid reservoir 24, and back to battery 28.

Figure 3:
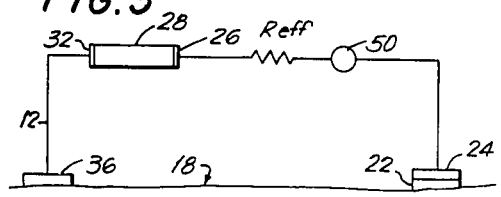
FIG. 3 is a schematic of electrical circuitry incorporated in the embodiment shown in FIGS. 1 and 2 showing an LCD indicator.

For a more particular description of the electrical circuit formed by the arrangement just described, reference is made to FIG. 3 wherein the circuit is shown schematically with numerals corresponding to the structure shown in FIGS. 1 and 2.

Battery 28 is connected through contact 32, cover 12, and adhesive layer 36 to skin 18. The other side of battery 28 is connected electrically through contact 26, liquid reservoir 24 and membrane 22 to skin 18 to complete the circuit. Resistor Reff represents the effective resistance of the complete circuit, including skin 18, the adhesive layer 36, cover 12, battery 28 and its contacts 26 and 32, as well as reservoir 24 and membrane 22. In a system of this type, one of the aims is to establish a very low specific rate of current flow so that the medicament will be deposited slowly over a long period of time. Current flow of down as low as 0.0001 ampere-hour per square centimeter of skin surface below membrane 22 is a typical current which may be selected for the application of a particular drug. Electrical resistance of the skin to current flow is of the order of 6–9 K ohms and is roughly independent of the distance between the points on the skin where electrical contact is made. This is because skin electrical resistance is largely that of resistance to penetration, the current flowing through the fluids of the body in which electrical resistance is very low. Thus, in order to establish current flow at the rate indicated, by Ohm's law, it is seen that total resistance of the circuit using a 1.5 volt battery should be about 360 K ohms for each square centimeter of application. This resistance, the effective resistance, Reff, of the circuit, can be built into any one component or combination of components of the circuit shown in FIG. 3, including the battery resistance, electrodes, cover material, etc. In addition, if desired, in order to maintain current flow constant over the full period of operation a constant current limiting device can be made integral with and a part of conductor 26, or any other part of the circuit where it is found convenient to do so.

Figure 4:
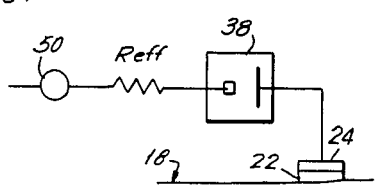
FIG. 4 is an alternative arrangement for the circuit shown in FIG. 3.

Furthermore, as indicated schematically in FIG. 4, applicator 10 may be designed to incorporate a provision to insure that the deposit of medicament will cease after a given period of time or after a certain quantity of drug is administered. This can be accomplished by inserting in the circuit an integrating device such as reverse plating cell 38. Cell 38, as is known in the art, comprises a pair of electrodes on which one is a coating of material to be transferred to the other electrode. When all of the plating material is deposited, after a predetermined period of time based upon the thickness of the original coating has lapsed, or integrated current flow representing the desired quantity of drug to be delivered, there is a large increase in internal resistance resulting in a substantial drop of current flow and an effective halt to drug migration. Such a device can be employed to establish in advance the period of time over which the medicamemt is to be applied or, as noted above, the quantity of the drug to be delivered. Cell 38 is a relatively high resistance device and could provide for much of the high resistance required for the operation of applicator 10.

Cell 38 may be made a part of contact 32 or be inserted between contact 32 and cover material 14. In addition, provision may be made for current flow to be built up gradually to avoid any shock to the recipient of the drug.

In FIGS. 1-4 there is shown liquid crystal display (LCD) 50 which is incorporated in the structure and circuitry of device 10. LCD 50 is designed so that it will cause a change in the light appearance only at and with the constant prescribed current of device 10. That is, with a completed circuit at such constant current, the prescribed dosage of medicament is being transcutaneously administered to the user, and LCD is light indicating so as to give a positive indication of this drug administration. In the event of (1) a broken circuit, such as a loosening of the conductive lip from the skin surface, (2) a dissipated or faulty battery, or (3) depletion of the medicament, so as to cause a failure of the constant current, the LCD will not show the liquid crystal display change, and the user will be informed that the prescribed drug is not being administered. The user is thus given a clear positive indication that either the drug is being properly administered or the drug is not being properly administered. In the latter event, the user merely removes the device and applies a new device, and upon the new application, the new LCD will be activated.

While the invention has hereinabove been described in the context of an LCD, light emitting diodes (LED) are also within the contemplation of this invention.

With the presence of indicator 50, the complete circuit is formed by skin 18, adhesive layer 36, cover 12, battery 28, indicator 50, contacts 32 and 26, filled reservoir 24, member 22 and resistor Reff.

Figure 5:
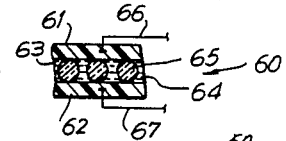
FIG. 5 is an enlarged sectional view of an alternate indicator embodiment.

Referring now to FIG. 5, there is shown a greatly enlarged sectional view of an alternate embodiment 60 for indicator 50. Indicator 60 comprises electroconductive polymeric upper and lower layers 61 and 62, respectively. Layers 61 and 62, in conjunction with non-conductive polymeric end caps (not shown), form a reserovir 63. Upper layer 61 has at least one transparent portion or is fully transparent for purposes hereinafter appearing. An electrochemically conductive phototropic material in the form of a solution or gel 64 is disposed in reservoir 63. A unilayer of silica particulates 65 disposed in reservoir 63 so as to provide non-conductive spacing for layers 61 and 63.

Electrical leads 66 and 67 are provided to complete the circuit with battery 28 and contact 24, respectively.

Electrochemically phototropic or electrochromic materials will change color or appearance with the passage of the current through the material. Reservoir 63 is filled with such color changing material which is viewable by the user through transparent upper layer 61. of the present device. Suitable electrochemical phototropic materials include, by way of example, those ion change sensitive indicator dyes as disclosed in U.S. Pat. No. 4,013,414, granted Mar. 22, 1977 to Lavalee et al. By providing a highly polar condition in the indicator of the present invention, such ion change sensitive indicator dye color variations would be detected, thereby informing the patient that the medicament is being administered.

A most preferred electrochromic indicator device for use in the present invention electrodes is that disclosed in U.S. Pat. No. 4,066,366, granted Jan. 3, 1978 to Zeller, which disclosure is incorporated herein by reference thereto.

It is also within the contemplation of the present invention that the device's constant current be utilized to effect a change in electromotive force, temperature or other kinetic energy on a chemical and/or dye material which is color-responsive or phototropic with such change, so as to serve as an indicator. Such suitable dye materials are, by way of example, disclosed in U.S. Pat. No. 4,362,645, granted Dec. 7, 1982 to Hof et al.

Applicator 10 may be prepared in advance, in different sizes and shapes, sealed within a plastic pouch, with a protective strip over its exposed side. Different drugs can be incorporated for particular applications, batteries may be varied to meet specific current flow requirements, and of course the electrical orientation of each battery would depend on the particular medicament. In the use of the device, the protective strip is removed and the applicator placed on the skin where desired, such as behind the ear.

Current flow starts immediately along with migration of the drug.

The use of the invention as herein described makes it possible for the first time to provide for drug therapy over an extended period of time with a degree of control and accuracy which heretofore has not been possible or practical. The cost of such therapy using this invention is reduced significantly with the result that extensive use of the invention will have a favorable economic impact on medical care. The indicator now provides a positive degree of assurance to the user not heretofore available in body worn medicament dispensers.

The indicator now provides a positive degree of assurance to the user not heretofore available in body worn medicament dispensers.

While only certain preferred embodiments of this invention have been described, it is understood that many embodiments thereof are possbile without departing from the principles of this invention as defined in the claims which follow.

What is claimed is:

1. A self-contained electrically powered drug applicator for the migration of medicament through the skin into the blood stream of a patient comprising: reservoir means containing said medicament forming a first electrode, battery means for charging/driving the medicament, means for covering comprising an electrically conductive material for partially enclosing at least said reservoir means leaving a side of said reservoir means exposed for contacting the skin, said cover means, being electrically connected to said battery means, and having a lip defining the periphery of said applicator and forming a second electrode for making contact with said skin when mounted on said skin leaving at least said reservoir means fully enclosed, and an electrically conductive adhesive material coating disposed on at least the underside of said lip, whereby when said applicator is adhered to said skin a complete electrical circuit between said first and second electrodes and through said skin is formed so as to drive said medicament out of said reservoir means and through said skin into the blood stream of said patient.

2. The applicator according to claim 1, in which said reservoir means is made from a microporous material whereby said medicament provides an electrical path therethrough.

3. The applicator according to claim 1, wherein said cover means and said reservoir means being thin in construction and conformable to the body.

4. The applicator according to claim 1, wherein said circuit having means to maintain constant current flow during the period said medicament is delivered.

5. The applicator according to claim 1, wherein said circuit having means to terminate deposition of said medicament after a predetermined quantity of medicament is delivered.

6. The applicator according to claim 5, said circuit including a reverse plating cell.

* * * * *